US012478755B2

(12) United States Patent
Nelson et al.

(10) Patent No.: US 12,478,755 B2
(45) Date of Patent: Nov. 25, 2025

(54) PATIENT INTERFACE WITH CONVERTIBLE CONNECTOR

(71) Applicant: Fisher & Paykel Healthcare Limited, Auckland (NZ)

(72) Inventors: Grant Leigh Nelson, Auckland (NZ); Carsten Ma On Wong Corazza, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/594,507

(22) Filed: Mar. 4, 2024

(65) Prior Publication Data

US 2024/0285891 A1 Aug. 29, 2024

Related U.S. Application Data

(63) Continuation of application No. 16/629,889, filed as application No. PCT/IB2018/055175 on Jul. 13, 2018, now Pat. No. 11,931,516.

(60) Provisional application No. 62/532,234, filed on Jul. 13, 2017.

(51) Int. Cl.

| | |
|---|---|
| ***A61M 16/08*** | (2006.01) |
| ***A61M 16/06*** | (2006.01) |
| ***A61M 39/20*** | (2006.01) |

(52) U.S. Cl.

CPC ........ *A61M 16/0816* (2013.01); *A61M 16/06* (2013.01); *A61M 16/0833* (2014.02); *A61M 16/0875* (2013.01); *A61M 39/20* (2013.01)

(58) Field of Classification Search

CPC .... A61M 16/0463; A61M 16/06-0622; A61M 16/0666; A61M 16/0816; A61M 16/0833; A61M 2039/1077; A61M 39/10; A61M 39/20

See application file for complete search history.

(56) References Cited

U.S. PATENT DOCUMENTS

| | | | | |
|---|---|---|---|---|
| 4,558,708 | A | 12/1985 | Labuda | |
| 5,701,886 | A * | 12/1997 | Ryatt | A61M 16/0816 128/203.29 |
| 6,209,539 | B1 | 4/2001 | Loescher | |
| 11,931,516 | B2 * | 3/2024 | Nelson | A61M 16/06 |
| 2004/0236311 | A1 | 11/2004 | Ishii | |

(Continued)

FOREIGN PATENT DOCUMENTS

| | | | |
|---|---|---|---|
| CN | 202105344 | U | 1/2012 |
| FR | 2935772 | B1 | 9/2010 |
| WO | WO 2014/109749 | A1 | 7/2014 |

OTHER PUBLICATIONS

International Search Report for International Application No. PCT/IB2018/055175 dated Sep. 17, 2018.

*Primary Examiner* — Joseph D. Boecker

(74) *Attorney, Agent, or Firm* — VIA LLP

(57) ABSTRACT

A patient interface comprises an opening for receiving a flow of gas from a conduit and an adaptable connector system for connecting at least two different types of conduit with the opening. The adaptable connector is permanently mounted with the patient interface so it cannot be lost and is able to swing into alignment with the opening, thereby providing a different connection end to be compatible with a second or further type of conduit connection end.

16 Claims, 9 Drawing Sheets

(56) References Cited

U.S. PATENT DOCUMENTS

| | | | | |
|---|---|---|---|---|
| 2008/0210242 | A1* | 9/2008 | Burk | A61M 16/06 128/206.21 |
| 2008/0251082 | A1 | 10/2008 | Sinha | |
| 2009/0260628 | A1 | 10/2009 | Flynn, Sr. | |
| 2011/0209709 | A1* | 9/2011 | Davidson | A61M 16/0816 128/205.25 |
| 2013/0199520 | A1* | 8/2013 | Dhuper | A61M 16/127 128/205.24 |
| 2014/0137860 | A1 | 5/2014 | Lanier | |
| 2016/0067438 | A1* | 3/2016 | Rollins, III | A61M 16/14 128/203.29 |
| 2020/0101255 | A1 | 4/2020 | Golub | |

* cited by examiner

PATIENT INTERFACE WITH CONVERTIBLE CONNECTOR

TECHNICAL FIELD

The invention relates to a patient interface and in particular a patient interface that features an adaptable connector system for connecting at least two different types of conduit configured for providing respiratory gas or gases.

BACKGROUND ART

Patient interfaces, e.g. in the form of a mask, are used to provide respiratory gas or gases, such as air in CPAP, VPAP, BiPAP, NIV or high flow rate therapy systems (e.g. at or above ambient pressure).

Commonly a patient interface of this type comprises a mask frame to which, for example, head gear attaches to hold the interface in position on the user's head when worn, and a seal module (sometimes also referred to as a cushion or cushion module) configured to couple to the mask frame and interface with a user's mouth and/or nose to deliver respiratory gases to the user. An interface may comprise a nasal, oral or oro-nasal (also referred to as full face) seal module. In turn, a patient interface may be an indirect interface which covers the nose, mouth, or both, or a direct interface such as an interface comprising nasal nozzles or pillows or similar which enter into and seal against or within the nares of the wearer or a cannula which non-sealingly enter the nares. The seal module can be formed entirely or almost entirely of a compliant material which is comfortable against the wearer's face, such as a silicone material, or the seal module may comprise a rigid or semi-rigid frame interfacing with part of a rigid or semi-rigid material which couples to the mask frame and a seal part formed of a relatively soft material.

Respiratory gases are delivered to the mask frame and seal module by a conduit that is usually connected via an elbow portion to the mask frame. The elbow may be fixed or articulated and includes an opening for connection with a connecting end of the conduit.

In order to form a sufficient seal to deliver respiratory gases the connections between the patient interface and conduit must be compatible. Accordingly, conduit connection ends for coupling with a patient interface are typically produced in standard sizes. However, there may be several different standard sizes used within a hospital or home environment. By way of example, compatible connector ends may be configured as a 22 mm male to couple with a 22 mm female taper. However, the size could be 15 mm or any other standard diameter or specific profile/shape. Connectors must have compatible geometries in order to provide an adequately secure fit.

If the connection end of a conduit and receiving connection opening of a patient interface do not match then an adapter would be needed to convert one connection end for connection to the other connection end. An adapter functions to downsize, upsize or otherwise modify the surface presented for connection so that the two components are compatible for coupling without leaking.

An adapter may be needed when a first gas source connected to the patient interface is required to be switched to a second gas source, i.e. a different conduit with a connection end different to the first gas source conduit. However, in practice, an adapter may not always be quickly to hand when a patient requires the gas source to be swapped over rapidly. Alternatively, gas sources can be swapped over by removing and replacing the entire mask associated with a particular gas source or treatment for one associated with a second or further gas source. Either scenario may lead to interruption to the required therapy due to delays and inconvenience when a gas source is required to be changed or, indeed, if a particular gas source conduit connection type happens to be incompatible with an available patient interface/mask.

SUMMARY OF THE INVENTION

It is an object of the present disclosure to provide one or more constructions that will go some way towards improving on the above or that will at least provide the public or the medical profession with a useful choice.

In a broad aspect the invention comprises a patient interface comprising an opening in the patient interface for receiving a flow of gas from a conduit, an adaptable connector system for connecting at least two different types of conduit connector ends with the opening, wherein the adaptable connector system is attached to the patient interface, the adaptable connector system having a first configuration in which the system is configured for connection of a first conduit type with the opening and the adaptable connector system has a second configuration in which the system is configured for connection of a second conduit type, different from the first type of conduit, with the opening.

The first and second conduit connection types could have different widths, geometries (e.g. oval or circle), taper, key/lock features, male/female connections or any of the foregoing alone or in combination. Attachment of the adaptable connector system to the patient interface could be by mounting, connection or a tether in order to combine the two components.

In an embodiment the adaptable connection system comprises a connector (alternatively and interchangeably termed 'adapter'), with at least two connection ends, mounted for movement relative to the opening, primarily so a connection end is alignable with the opening. The movement may involve pivoting, swivelling, rotating, revolving or swinging. The connector is preferably tubular and can be broadly described as a convertible connector since it converts the opening to the patient interface from a first to second configuration to couple with different conduit connector ends and back.

In an embodiment the connector is attached for movement, e.g. by an extending arm between the connector and patient interface. The connector is preferably attached by the arm for pivoting movement relative to the patient interface by a pivot axis, said pivot axis being perpendicular to a central axis of the opening. Preferably at least the connection end of the connecter facing the opening is able to be concentrically aligned with the opening. For example, the arm extends from a position adjacent the opening to a side wall of the connector to enable concentric alignment. Preferably the connector is additionally able to be moved in an axial direction relative to the opening, e.g. the point at which the connector pivots includes a slot or channel for slidably receiving a pivot pin for enabling axial movement of the connector relative to the opening while concentrically aligned.

In an embodiment a mounting portion of the adaptable connector system with the opening may comprise a connection tube that is mounted for swivelling movement relative to the patient interface, i.e. about a central axis of the opening, since both the connection tube and patient interface's opening are annular and concentrically aligned. Such a connection tube allows the connector to swivel relative to the patient interface, as well as pivot perpendicularly to the swivel axis.

In one embodiment of the invention the adaptable connector system comprises a first connection associated with the opening and the connector or adapter is mounted by the arm for swinging movement relative to the patient interface for removable attachment to the first conduit connection to change the system from the first configuration to the second configuration. The connector has at least a second conduit connection end that provides the second configuration. Preferably the arm enables swinging movement of the connector by virtue of a pivot axis between an end of the arm distal from the connector and the patient interface.

In another embodiment the connector has additional connector ends. For example, a third connection end which is compatible with a further conduit connector type. During normal use the connector will be a bridge between the opening and a conduit connector end such that any unused (e.g. third or fourth) connection end should have some kind of closure or peripheral attachment, e.g. by a plug, valve, pressure gauge, filter, second gas source, one-way valve.

In a further embodiment the adaptable connector system comprises an adaptor or connector mounted from the patient interface that is configurable to be connected to the opening by either of a first or second end to change the system from the first configuration to the second configuration. Preferably the arm enables rotating movement of the connector about an axis through an end of the arm (e.g. spanning between a pair of arms) distal from the patient interface and through a midpoint of a sidewall of the connector (e.g. where the connector is mounted for rotation about the axis between the pair of arms). The axis of rotation is perpendicular to a central axis of the opening. In this way the connector can be inverted or rotated 180 degrees to present a first connection end or a second connection end for connection to the opening or vice versa. The opposite end is presented for connection to a compatible conduit connection to establish communication with a gas source.

In a particular embodiment the connector is able to be rotationally moved relative to the opening, e.g. by providing a joining slot or channel perpendicular to the slot or channel enabling movement in the direction of the central axis. Such a structure resembles a bayonet fitting where a pivot pin slides in the slot and then perpendicularly to axially lock the connector relative to the opening of the patient interface.

Interfaces of the invention may be used in continuous positive airway pressure (CPAP) systems for providing a heated and optionally also humidified air stream to a user through the interface worn by the user, or alternatively in other forms of respiratory systems, such as for example VPAP (variable positive airway pressure) systems, BiPAP (bi-level positive airway pressure) systems, or in non-invasive ventilation (NIV), or high flow rate (not necessarily also above ambient pressure) therapy and are described herein generally with reference to CPAP therapy by way of example only.

In the specification the term "comprising" means "consisting at least in part of". When interpreting a statement in this specification and claims that includes "comprising", features other than that or those prefaced by the term may also be present. Related terms such as "comprise" and "comprises" are to be interpreted similarly.

BRIEF DESCRIPTION OF THE DRAWINGS

Embodiments are described with reference to the accompanying drawings, by way of example and without intending to be limiting, in which.

DETAILED DESCRIPTION OF SPECIFIC EMBODIMENTS

Figure 1:
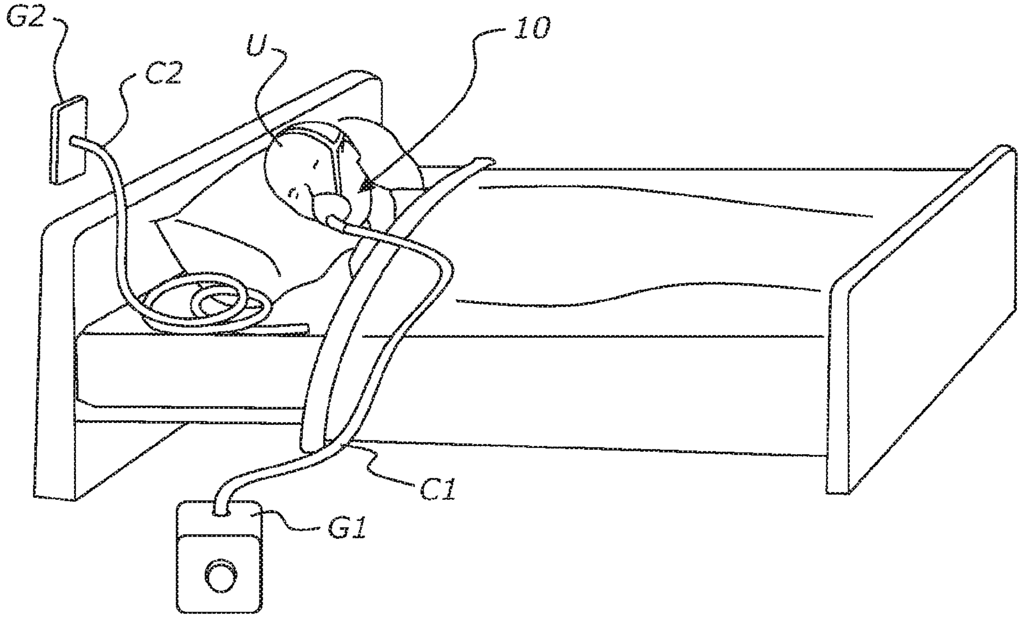
FIG. 1 is a perspective view of a patient interface for delivering respiratory gases from, potentially, two or more conduit types.

A general use scenario for a patient interface according to the invention is illustrated by FIG. 1. A patient interface 10 will be fitted to the face of a user U and connected to a gas source G1, e.g. a CPAP device, by a flexible conduit C1. In some cases it may be necessary to switch to a second gas source G2, e.g. a wall mounted gas line, delivered through a second conduit C2. The precise use scenario is not necessarily depicted by FIG. 1 as there will be a variety of possible reasons why different conduits C1, C2 are required to be connected to a patient interface.

The purpose of the invention is to address the situation where the respective connector ends of conduits C1 and C2 (not shown in detail in the drawings) are different. Ordinarily, an opening to patient interface 10 will only be provided with a single connector type, compatible with a single type of conduit connector end. When the connectors are not compatible it will be necessary to employ an adapter or change the patient interface entirely in order to be compatible with the new conduit connector end, e.g. switching from C1 to C2.

Figure 2:
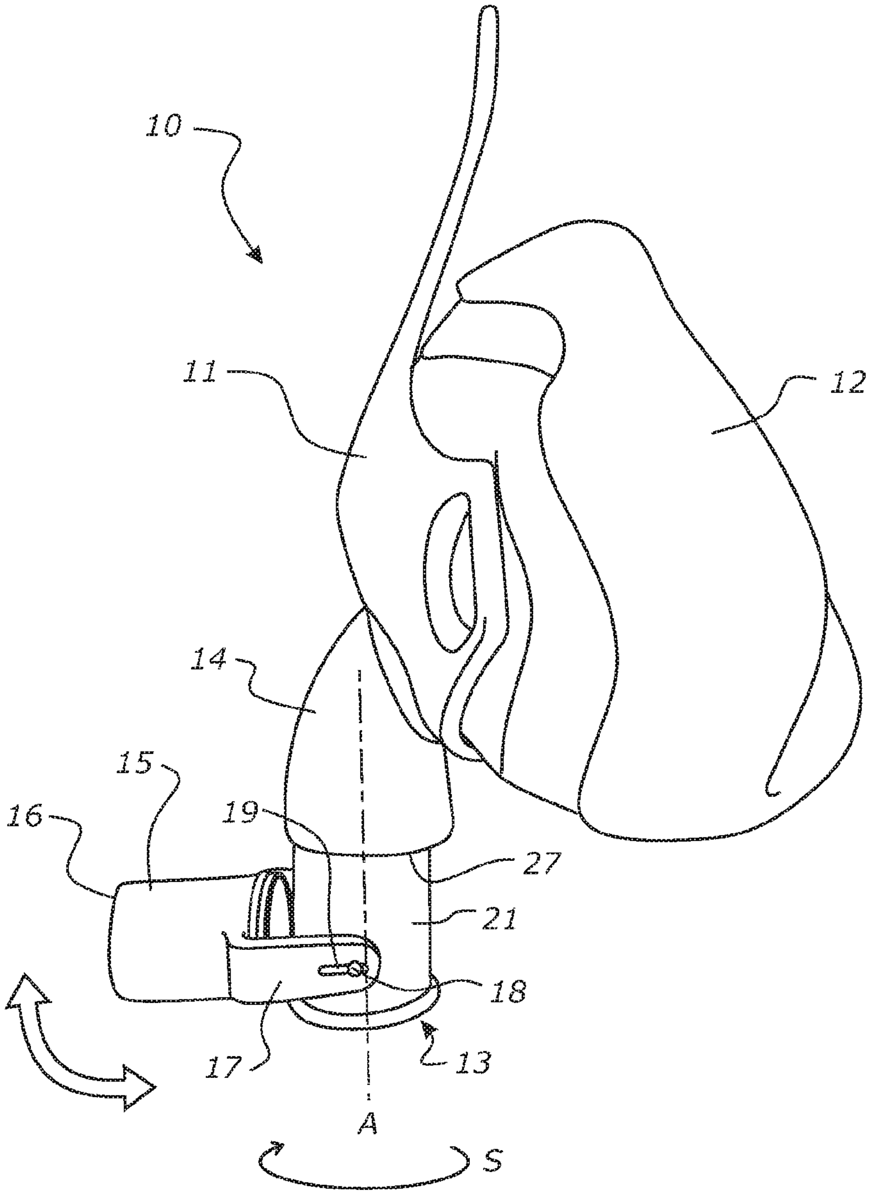
FIG. 2 is a side elevation view of a first embodiment of patient interface comprising a mask frame and seal module, with a connector mounted for rotating movement relative to an opening in the mask frame.
Figure 3:
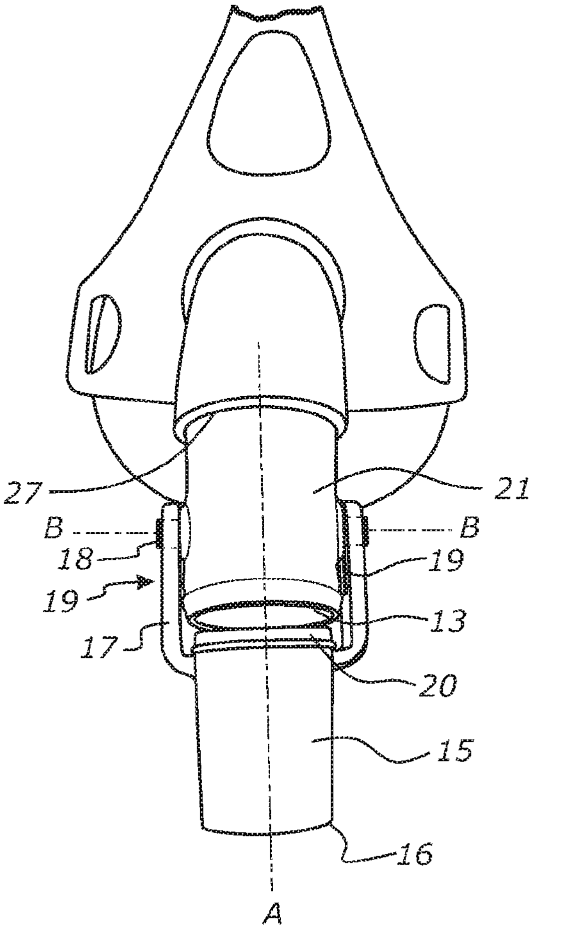
FIG. 3 is a front elevation view of the patient interface from FIG. 2, where the connector has been rotated 90 degrees, in a position just prior to engagement with the opening.
Figure 4:
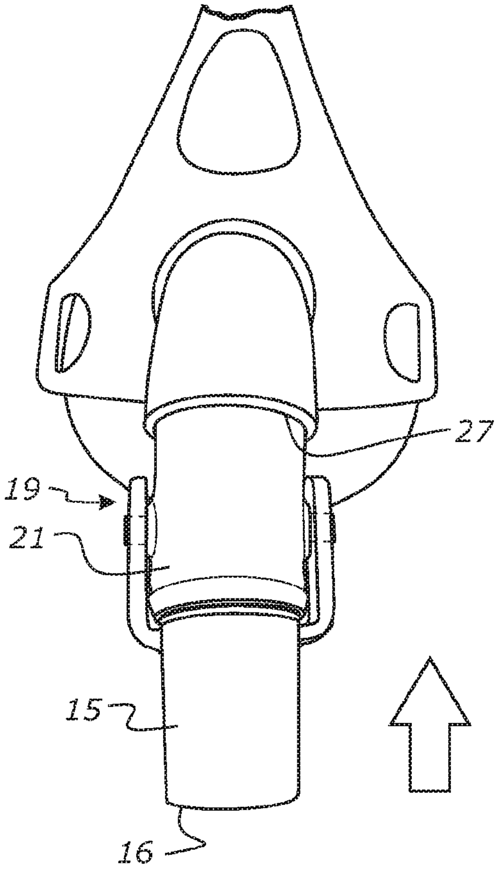
FIG. 4 is a front elevation view where the connector has been engaged with the opening to the patient interface.

FIGS. 2 to 4 illustrate a first embodiment according to the invention. The patient interface is generally denoted 10 and includes a mask frame 11 coupled with a seal module 12. The exact configuration of the patient interface is not an essential aspect of the present disclosure, for example it may take many forms such as including a face seal that is permanently integrated with the frame. The seal module may be full face, full face over nose, full face under nose, nasal or oral. The present invention is concerned with an opening end 13 which provides a pathway into the patient interface 10 to deliver respiratory gases. Opening 13 is usually located at the distal end of an elbow 14 moulded with the mask frame or in an articulated but sealed arrangement therewith.

Opening 13 may be located at the end of a separate connector tube 21 from the patient interface, to be coupled to elbow 14 by a swivel connection 27 about a central axis A of opening 13. Swivelling movement is indicated by a directional arrow S. Connector tube 21 could be demountable from elbow 14 or fixed in the axial direction. Indeed, this component 21 could be screw threaded upon a receiving portion of elbow 14 and replaceable with alternative configurations if needed. Alternative configurations could include a friction fit, bump fit, snap fit, threaded or unthreaded.

Opening 13 (or connector tube 21) ordinarily includes a connection end of a standard size, to be compatible with the connection end of a conduit it is recommended for use with. Therefore, if the connection end of a conduit (not illustrated in FIGS. 2 to 4) is otherwise compatible with the connection opening 13 of the patient interface then these components can be connected in the normal way and gas delivery can begin once the patient interface is fitted to a user.

In the case where an incompatible conduit connector end is to be connected with connector opening 13, an adapter would ordinarily be required to bridge between the non-matching connector parts.

Referring to FIG. 2, the patient interface's connection opening 13 can be described as a first connection end, while a separate converting connector (or interchangeably termed 'adapter') 15 is provided, in an un-deployed state according to FIG. 2, serving to provide a second connector end 16 having different relative dimensions or mating characteristics than the first connector end 13.

Converting connector 15 is mounted by a pair of extending arms 17 for pivoting about an axis B, perpendicular to centre axis A associated with opening 13. The pivoting motion is enabled by a pair of pivot pins 18 extending from a side wall of the elbow 14 or connector tube 21, captured by a slot 19 formed at an end of arm 17 distal from converting connector 15. The nature of the pivot could be relatively loose or provide an interference fit between pin 18 and slot 19 so that the converting connector 15 generally holds its swing position, i.e. in a raised position as illustrated in FIG. 2 or in a lowered/deployed position as illustrated in FIGS. 3 and 4.

Referring now to FIGS. 3 and 4, it will be apparent that the converting connector 15 has swung into a position where said connector is generally concentrically aligned with first connector end opening 13. However, at least initially, converting connector 15 is in a position spaced apart from opening 13 where an air gap is present. To close this gap, connector 15 is pushed in the direction of axis A towards opening 13 so that its facing compatible connection end 20 engages therewith. Coaxial longitudinal movement along axis A is enabled by the provision of slot 19 permitting sliding movement of pivot pin 18 between first and second positions. Connector 15 is generally held in engagement by a taper fit between the patient interface compatible end 20 and opening 13. As an example, opening 13 may be a 22 mm female opening, while the mating end 20 of converting connector 15 is a 22 mm tapered male connection.

In the illustrated embodiment of FIGS. 2 to 4 the outermost second connection end 16 of converting connector 15 is the same type as its innermost, opposite, end 20. In the illustrated form the connection end 16 presented to a conduit connection end (not shown) has been converted from a female tapered opening 13 (as in FIG. 2) to a male part receivable by a like-sized female part (FIG. 4) of a conduit connector (not shown).

In other words, a patient interface may be converted from a first configuration (FIG. 2) that is able to receive a male mating connection end of a conduit, to a second configuration (FIG. 4) able to couple with a compatible female connection end of a conduit. The connection type could be a taper fit, friction fit, snap fit, bump fit or other variation known in the art.

It will be apparent that alternative connection types are possible at end 16 that employ the same principle of providing a converting connector/adapter that is mounted with the patient interface but movable into place when needed. Adaption/conversion types include male to male, female to female, male to female, female to male; each with different relative dimensions or mating characteristics.

Figure 13:
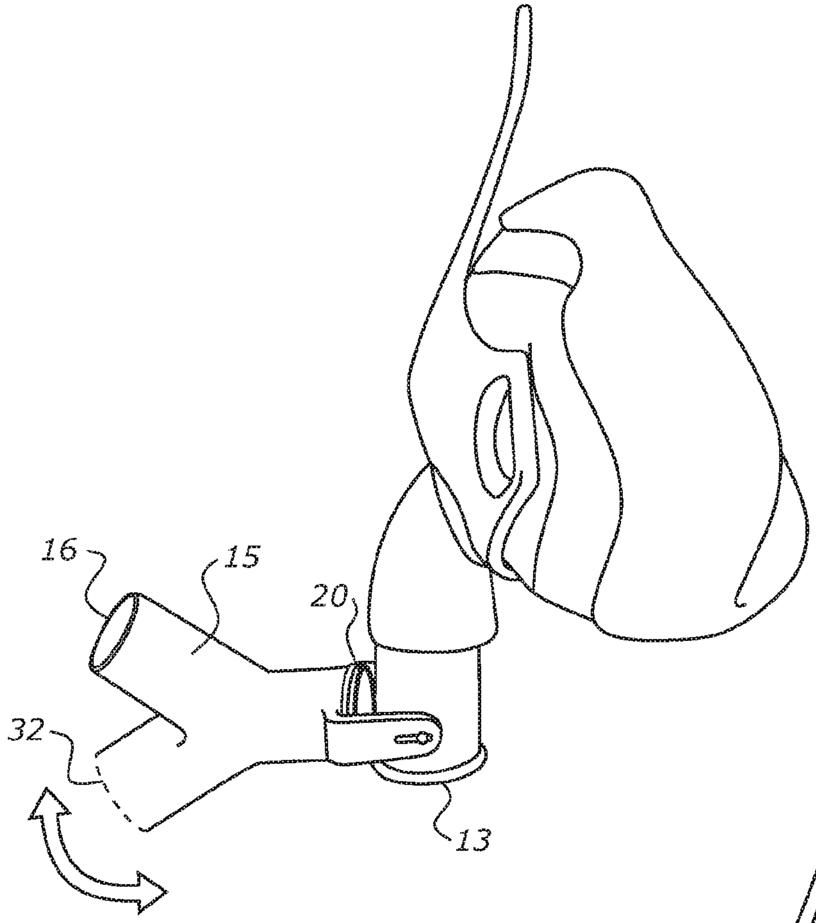
FIG. 13 is a perspective view of a fourth embodiment, based on the first embodiment of FIGS. 2 to 4, wherein a further connection end is provided.
Figure 14:
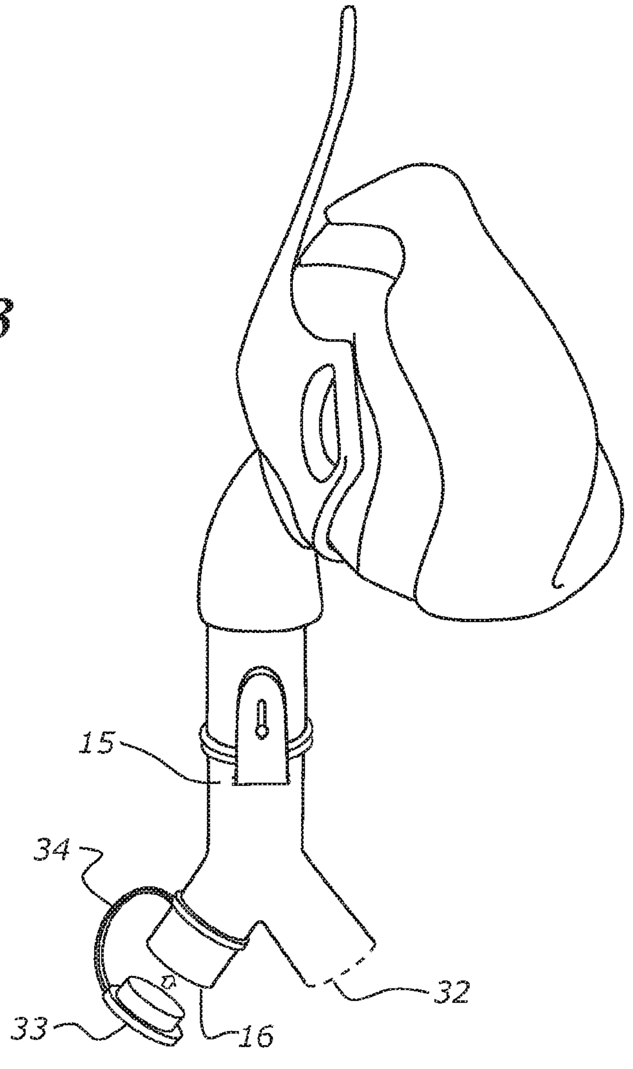
FIG. 14 is a further view of the fourth embodiment wherein the connector is deployed.

A variation on the first embodiment is shown by FIGS. 13 and 14 which provides a converting connector 15 with a further opening 32, different from second connection end 16, thereby providing an alternative connection option and an appearance, when in a deployed position of FIG. 14, of an inverted Y junction connector. The mating end 20 of connector 15 which aligns with opening 13 maintains a compatible connection type with opening 13, but outer connection ends (16 and further end 32) may have other characteristics, dependent upon the required types of conduit utilised. Connection end 32 is depicted in dotted detail to represent that it could take any suitable connection type-form, e.g. a taper fit the same or different to end 16, a friction fit, snap fit, bump fit, symmetrical or asymmetrical geometry. FIGS. 13 and 14 show, while second connection end 16 in FIG. 2 is coaxial along axis A, connector 15 can branch off in other directions.

According to this modified embodiment, once converting connector 15 is sealed with the patient interface and a conduit connection end, any open connection end should preferably have a closure, e.g. by a plug 33. However, other closures or connections are possible such as a one way valve, pressure gauge, filter, and/or second gas source. Any suitable closure or connection may be employed, and could be attached by a flexible tether 34 to prevent loss, e.g. a cap/plug 33 connected by a cable or the like tying it to the patient interface.

FIGS. 5 to 8 illustrate an alternative embodiment of the invention. In the illustrated form mounting arms 17 extend from the patient interface side adjacent elbow 14 and first connection end 13. The arms 17 are located on opposed sides of the elbow 14. The converting connector 25 is supported between mounting arms 17 by pivot pins 28 that extend from a side wall of converting connector 25 to create a rotating axis B that is perpendicular to centre axis A of opening end 13 of the patient interface.

Figure 5:
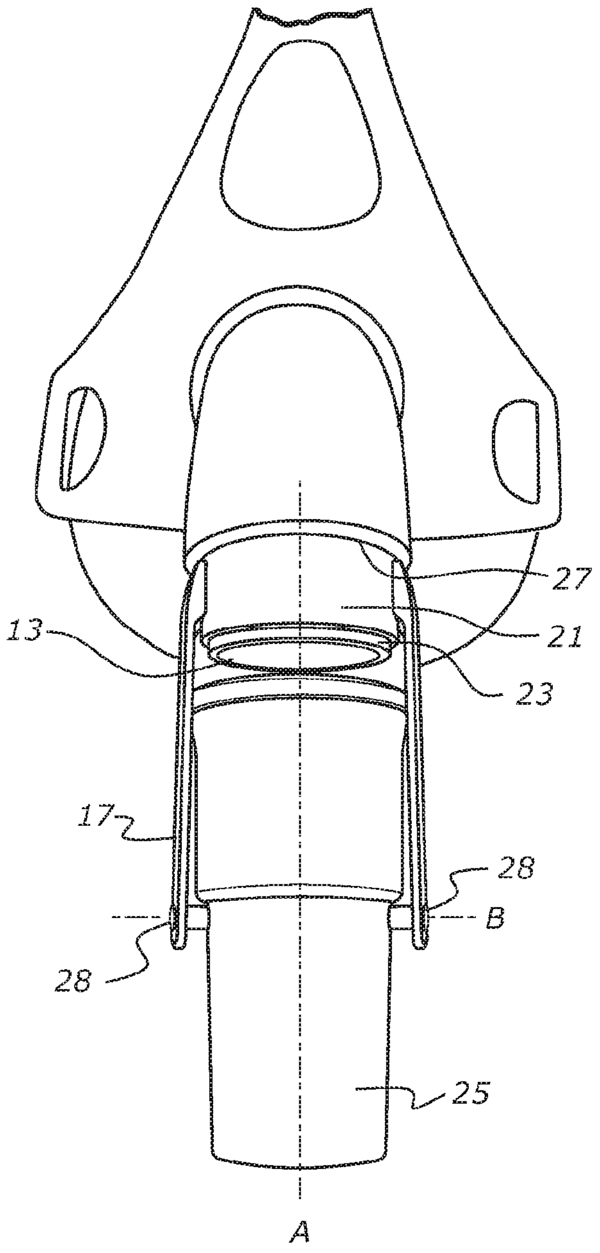
FIG. 5 is a front perspective view of a second embodiment of the invention.
Figure 6:
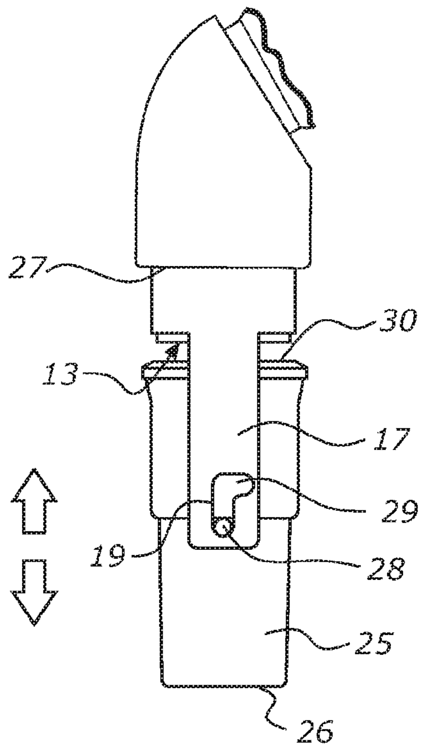
FIG. 6 is the first in a sequence of reconfiguring a connector between a first and second configuration according to the second embodiment.

It will be apparent that FIGS. 5 and 6 illustrate converting connector 25 in an unconnected state relative to opening 13.

However, it will also be apparent that a first converter end 30 of converting connector 25 can be coupled with opening 13 in order to form a seal therewith. First converter end 30, in the illustrated form, is a female connecting part for receiving a tapered male part associated with or surrounding opening 13. Engaging movement along axis A is possible by virtue of an elongate channel 19 which support pivot pins 28 able to slide therein, either freely or in an interference fit arrangement.

Figure 7:
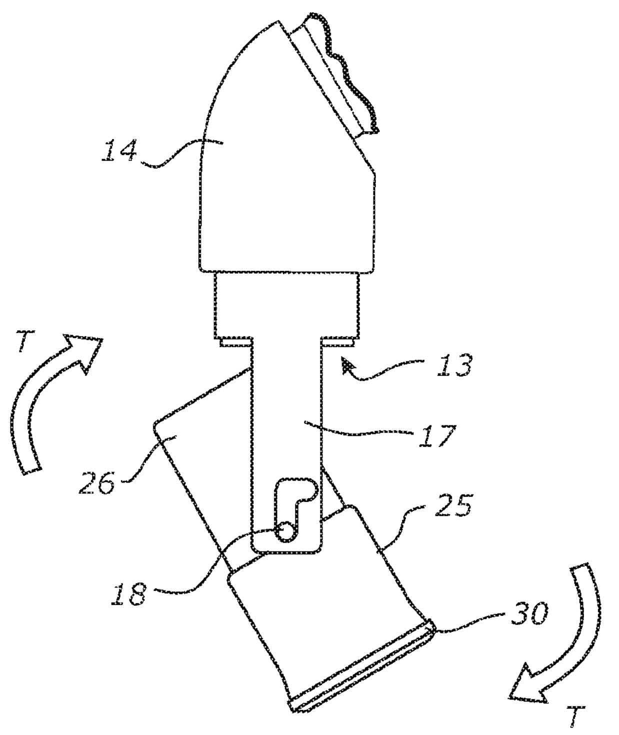
FIG. 7 is the second in a sequence of reconfiguring a connector between a first and second configuration according to the second embodiment.

When in a disengaged position as illustrated by FIGS. 5 and 6, the converting connector 25 is free to rotate about axis B indicated by directional arrows T. FIG. 7 shows converting connector 25 moving out of concentric alignment with opening 13 to an intermediate position where converting connector 25 has spun clockwise and effectively moved first converter end 30 to a distal orientation while a second converter connection end 26 moves into a near orientation relative to the patient interface opening 13.

Figure 8:
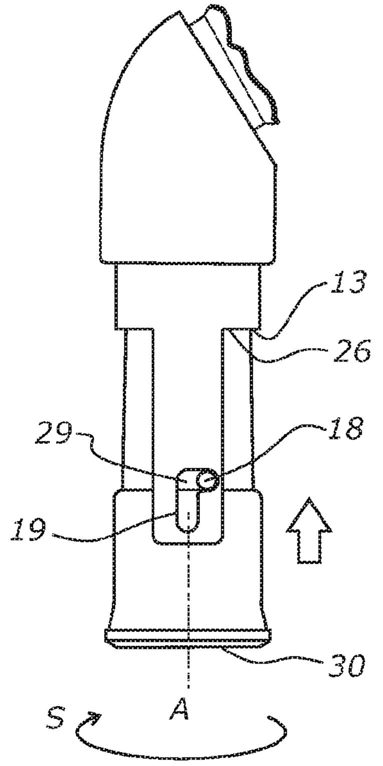
FIG. 8 is the third in a sequence of reconfiguring a connector between a first and second configuration according to the second embodiment.

Concentric alignment along axis A is restored according to FIG. 8 that further illustrates a second engaged state where converting connector 25 is moved along axis A towards opening 13, thereby engaging second converter end 26 therewith in a sealing arrangement. A seal can be further secured by twisting converting connector 25 about centre axis A such that pivot pin 18 moves into a perpendicular branch 29 of slot 19 in a bayonet-type fitting arrangement, such as illustrated by FIG. 8. Twisting movement is indicated by the same swivel directional arrow S. A bayonet fitting arrangement is not necessarily essential but improves security by reducing the chance of the connector being accidentally pulled out of place. A sufficient taper fit or other secure connection, such as a snap fit or clip could provide an alternative or supplement the bayonet fitting.

The total arrangement shown in stepwise form by FIGS. 6 to 8 has effectively transitioned between a first connection configuration (end 30 engaged with opening 13 while end 26 is available to connect with a first conduit connection type) shown by FIG. 6 to a second connection configuration (end 26 engaged with opening 13 while end 30 is available to connection with a second conduit connection type) shown by FIG. 8.

The configuration can be reversed by disengaging end 26 from opening 13 by virtue of the bayonet connection 29 and flipping converting connector 25 about axis B, thereby returning converter end 30 to be facing opening 13 for re-engagement.

As best seen in FIG. 5, opening 13 may include one or more connecting features 23 in order to be compatible with both first converter end 26 and second converter end 30. In the illustrated form opening 13 includes a protruding annular flange 23 on an inner surface that is configured to engage within the male mating end 26. In this sense opening 13 has both male and female mating features in order to be more universally compatible with both ends of converting connector 25.

Figure 15:
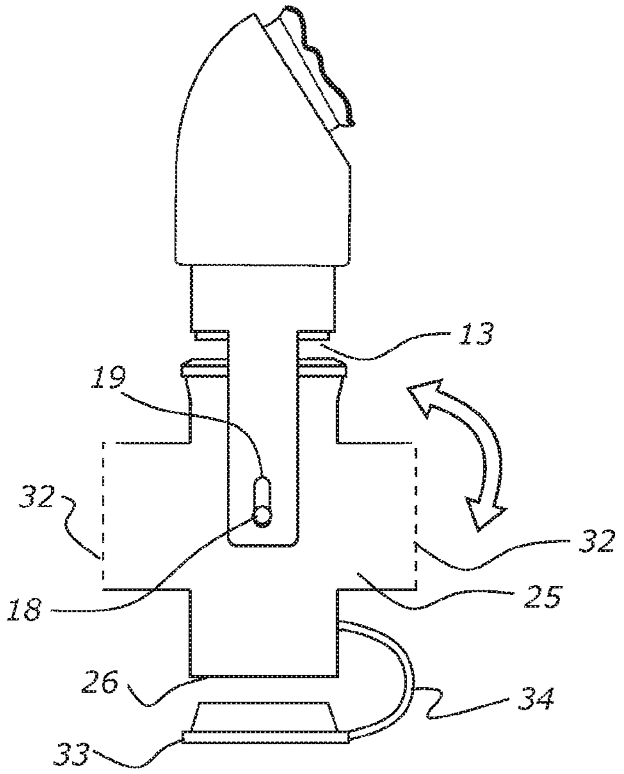
FIG. 15 is a side view of a fifth embodiment, based on the second embodiment of FIGS. 5 to 8, wherein further connection ends are provided.
Figure 16:
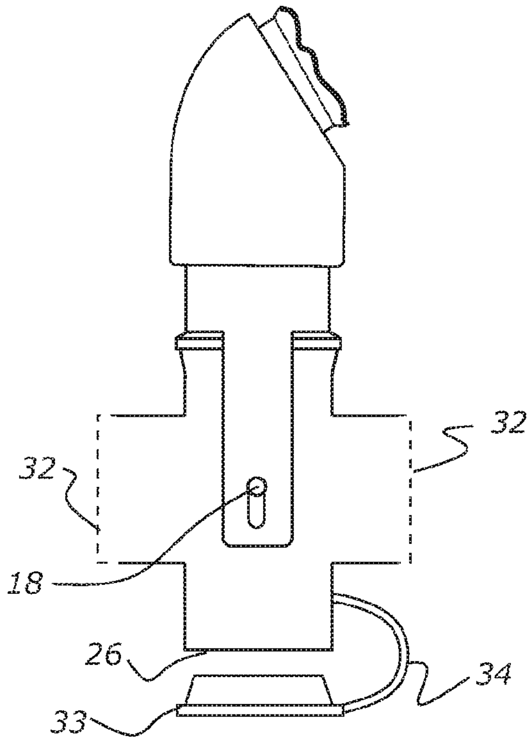
FIG. 16 is side view of the fifth embodiment from FIG. 15, in an engaged position.

In a further embodiment illustrated by FIGS. 15 and 16 the converting connector 25 may be provided in a Y or X configuration, i.e. that has three or four available connection ends in addition to the opening 13. FIGS. 15 and 16 show a four connection end option in a deployed and non-deployed position respectively. Each end 16, 30, 32 must be compatible with opening 13 but could have additional features to ensure compatibility with multiple conduit connector types, depicted by a dotted line to represent multiple possibilities for connection-type 32, e.g. a taper fit the same or different to end 26 or 30, a friction fit, snap fit, bump fit, symmetrical or asymmetrical geometry. A bayonet fitting is less practical in such a configuration however pivot pin 18, sliding within a slot 19, may still be employed. Preferably a more secure taper or other type of fitting (e.g. snap fit, clip, locking feature) is provided to couple opening 13 and a respective connecting face 26, 30, 32.

Figure 9:
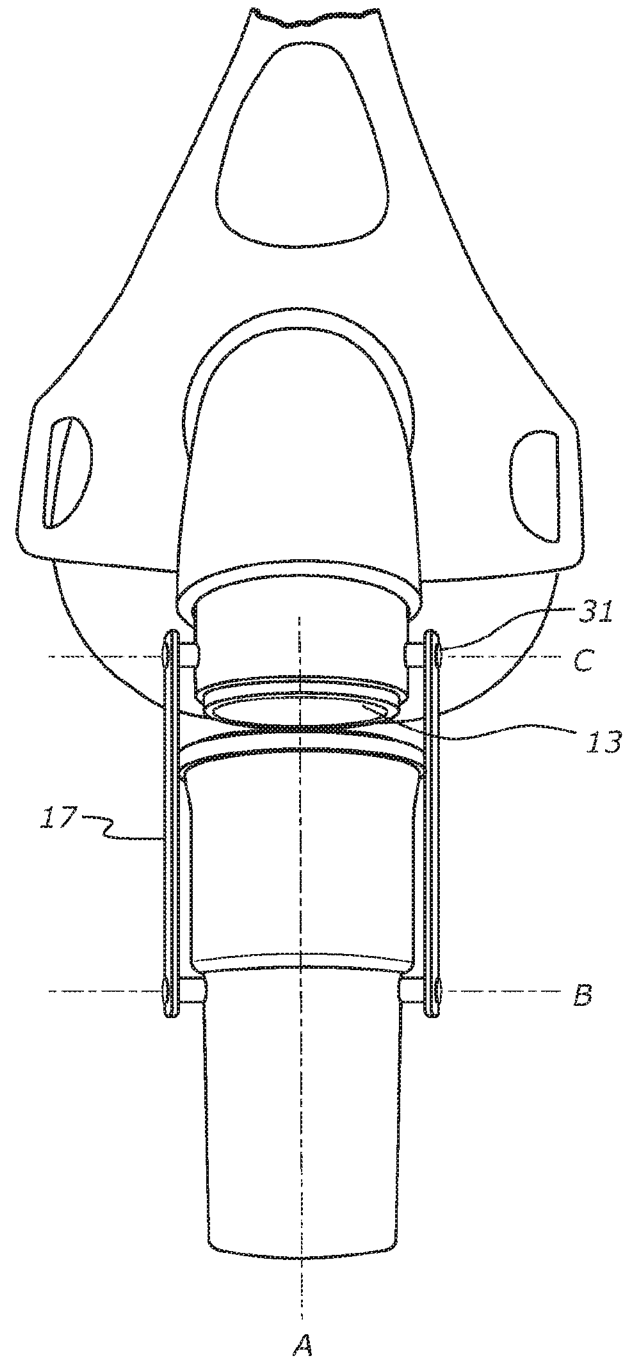
FIG. 9 is a front perspective view of a third embodiment of the invention.
Figure 10:
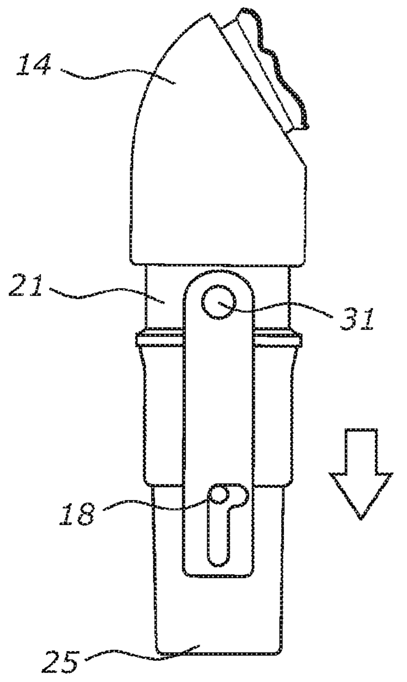
FIG. 10 is the first in a sequence of reconfiguring a connector between a first and second configuration according to the third embodiment.
Figure 12:
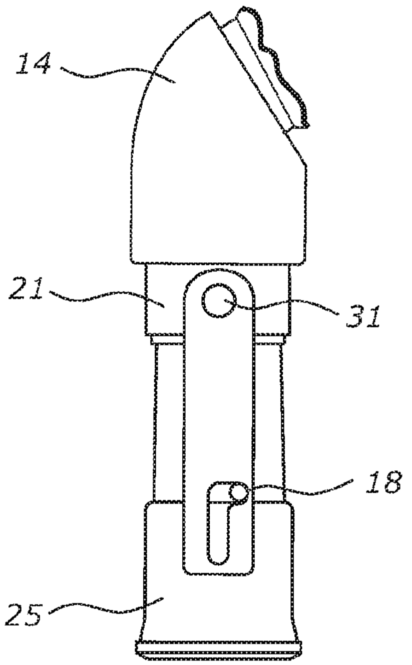
FIG. 12 is the third in a sequence of reconfiguring a connector between a second and third configuration according to the third embodiment.
Figure 11:
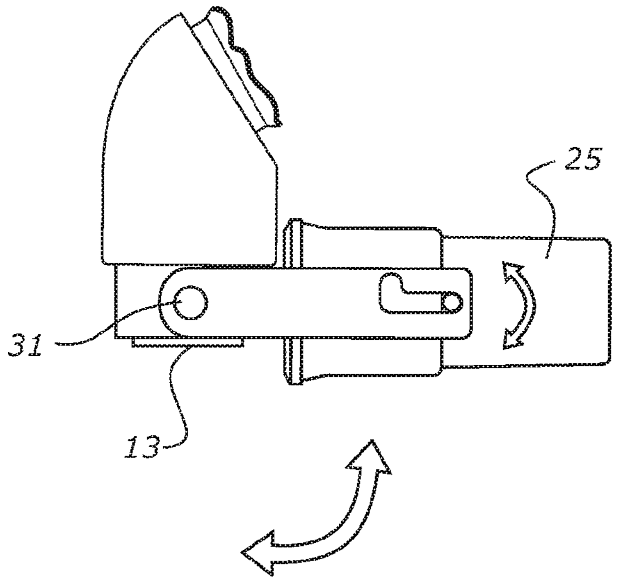
FIG. 11 is the second in a sequence of reconfiguring a connector between a first and second configuration according to the third embodiment.

FIGS. 9 to 11 illustrate a third embodiment that effectively combines features from the first and second illustrated embodiments described above. General aspects of the double-ended rotatable converting connector 25 from FIGS. 5 to 8 are preserved with the addition of a set of pivot pins 31 extending from a side wall of the patient interface adjacent the elbow 14 and/or connector tube 21 that enable arms 17 to swing about an axis C, parallel to axis B and perpendicular to centre axis A of the opening 13. As is clearly visible by FIG. 11 pivot pins 31 allow the arms supporting converting connector 25 to swing out of the way of opening 13 in order to expose this opening as a means of direct connection with a conduit connector (not illustrated). In principle, the embodiment of FIGS. 9 to 11 enables three types of connection compatibility with an external conduit connector. Combining this embodiment with the embodiment of FIGS. 15 and 16 potentially enables five connection types since a four way connector may be coupled with or moved out of the path of opening 13.

Further configurations of the invention may be possible without departing from the scope of the appended claims. For example, the ability of the adaptable connector system to swivel about axis A can be incorporated into all embodiments to provide further flexibility when connecting a conduit therewith. A conduit may have an inherent spring bias twisting in a particular direction by virtue of its construction which can be alleviated by a swivel connection to reduce stress and the possibility of a taper fit coming loose.

Pivot pins 18, 31 while illustrated as extending from the patient interface connector 21 (FIG. 2) or converting connector 25 (FIG. 5) could alternatively be formed as extensions from the arms 17 for receipt by a hole or slot formed in the surface of the connector 21 or converting connector 25.

Available manufacturing techniques may produce the components described herein as separate or integrated parts depending on requirements.

The invention claimed is:

1. A patient interface comprising:

an opening for receiving a flow of gas from a conduit, the opening comprising a tubular opening end and an annular flange protruding from the tubular opening end; and a connector coupled to the patient interface, the connector comprising a first end having a first conduit connector end type and a second end having a second conduit connector end type;

wherein:

the annular flange of the opening is configured to be selectively engageable with the first end of the connector and the second end of the connector, and the connector is coupled to the patient interface such that it is selectively transitional between:

a first configuration, wherein the annular flange is engaged with the first end of the connector, and a second configuration, wherein the annular flange is engaged with the second end of the connector.

2. The patient interface of claim 1, wherein:

the first conduit connector end type of the first end is a female connector end type; and the second conduit connector end type of the second end is a male connector end type.

3. The patient interface of claim 2, wherein the annular flange is configured such that:

in the first configuration, the annular flange receives the first end of the connector within the annular flange; and in the second configuration, the annular flange is received within the second end of the connector.

4. The patient interface of claim 1, wherein the connector is coupled to the patient interface by a pair of arms that attach the connector for movement relative to the opening.

5. The patient interface of claim 4, wherein the connector comprises a pair of pins extending outwardly from the connector along an axis, wherein a first pin of the pair of pins is engaged with a first opening in a first arm of the pair of arms, and a second pin of the pair of pins is engaged with a second opening in a second arm of the pair of arms.

6. The patient interface of claim 5, wherein the connector is rotatable relative to the patient interface about the axis.

7. The patient interface of claim 6, wherein the first opening and the second opening each comprise slots configured such that the first pin and the second pin can each move translationally along a length of the slots.

8. The patient interface of claim 7, wherein the slots comprise L-shaped slots.

9. The patient interface of claim 4, wherein the connector is coupled, via the pair of arms, for rotational movement relative to the opening.

10. The patient interface of claim 9, wherein the connector is coupled, via the pair of arms, for displacement relative to the opening in a direction along an axis of the opening.

11. The patient interface of claim 1, wherein the annular flange is configured for connection to a compatible connector end of a conduit in addition to the first end of the connector and the second end of the connector.

12. The patient interface of claim 1, wherein the connector is mounted by a bayonet fitting to seal communication between one of the first end of the connector and the second end of the connector and the annular flange.

13. The patient interface of claim 1, wherein the first and second conduit connector end types each comprise different features selected from one or more of the following alone or in combination: widths, geometries, taper, key or lock features, male or female connections, or coupling elements.

14. The patient interface of claim 1, wherein the connector further comprises at least a third end that is selectively engageable with the annular flange of the opening in addition to the first end and the second end.

15. The patient interface of claim 14, further comprising a closure for closing one or more of the first end, the second end, and the third end.

16. The patient interface of claim 15, wherein the closure is tethered to the patient interface.

* * * * *